United States Patent
Honmou et al.

(10) Patent No.: US 12,110,480 B2
(45) Date of Patent: Oct. 8, 2024

(54) OBSERVATION DEVICE

(71) Applicants: NIPRO CORPORATION, Osaka (JP); SAPPORO MEDICAL UNIVERSITY, Sapporo (JP)

(72) Inventors: Osamu Honmou, Sapporo (JP); Daiki Tateyama, Osaka (JP); Kosuke Takahashi, Osaka (JP); Kosei Tateyama, Nasushiobara (JP); Yoshihiro Yoshikawa, Osaka (JP)

(73) Assignees: NIPRO CORPORATION, Settsu (JP); SAPPORO MEDICAL UNIVERSITY, Sapporo (JP)

( * ) Notice: Subject to any disclaimer, the term of this patent is extended or adjusted under 35 U.S.C. 154(b) by 733 days.

(21) Appl. No.: 17/256,362

(22) PCT Filed: Jul. 4, 2019

(86) PCT No.: PCT/JP2019/026633
§ 371 (c)(1),
(2) Date: Dec. 28, 2020

(87) PCT Pub. No.: WO2020/009186
PCT Pub. Date: Jan. 9, 2020

(65) Prior Publication Data
US 2021/0271062 A1    Sep. 2, 2021

(30) Foreign Application Priority Data
Jul. 6, 2018    (JP) .................................. 2018-129146

(51) Int. Cl.
*C12M 1/34*    (2006.01)
*C12M 1/00*    (2006.01)
(Continued)

(52) U.S. Cl.
CPC ............ *C12M 41/36* (2013.01); *C12M 23/22* (2013.01); *C12M 23/34* (2013.01); *C12M 41/12* (2013.01);
(Continued)

(58) Field of Classification Search
None
See application file for complete search history.

(56) References Cited

U.S. PATENT DOCUMENTS 5,989,835 A * 11/1999 Dunlay .................. G02B 21/16
977/881
6,548,263 B1 * 4/2003 Kapur .................. B01J 19/0046
216/2
(Continued)

FOREIGN PATENT DOCUMENTS

| CN | 104862226 A | 8/2015 |
|---|---|---|
| EP | 2428792 A1 | 3/2012 |

(Continued)

OTHER PUBLICATIONS

Ishmukhametov, R. et al., "A Simple low-cost device enables four epi-illumination techniques on standard light microscopes", Scientific Reports, 6, 20729, pp. 1-13; Feb. 8, 2016.

*Primary Examiner* — Derek S. Chapel
(74) *Attorney, Agent, or Firm* — Jordan and Koda, PLLC; Steven P. Koda, Esq.

(57) ABSTRACT

An observation device includes a microscope. The microscope includes an illumination light beam source, an illumination optical system, and an observation optical system forming an optical image of an observation target from reflected light beams obtained by reflection of illumination light beams by the observation target. The observation optical system includes a phase plate changing the phase of directly reflected light beams reflected on a reflection surface among the reflected light beams. Both the illumination
(Continued)

optical system and the observation optical system are arranged under the observation target. The observation device includes an image pickup device photoelectrically converting the optical image obtained by the observation optical system to create image data of the observation target and a display device displaying the image data. The illumination light beam emitted from the illumination optical system is a collimated light beam.

11 Claims, 4 Drawing Sheets

(51) Int. Cl.
*G02B 21/08* (2006.01)
*G02B 21/14* (2006.01)
*G02B 21/26* (2006.01)
*G02B 21/36* (2006.01)
*G06V 20/69* (2022.01)

(52) U.S. Cl.
CPC ........... *G02B 21/082* (2013.01); *G02B 21/14* (2013.01); *G02B 21/26* (2013.01); *G02B 21/365* (2013.01); *G06V 20/693* (2022.01); *G06V 20/695* (2022.01)

(56) References Cited

U.S. PATENT DOCUMENTS

| | | | |
|---|---|---|---|
| 2007/0177255 | A1 | 8/2007 | Kanegasaki et al. |
| 2008/0247038 | A1* | 10/2008 | Sasaki ............... G02B 21/0088 |
| | | | 359/395 |
| 2015/0346474 | A1* | 12/2015 | Iguchi ............... G02B 21/0032 |
| | | | 359/385 |
| 2016/0025959 | A1 | 1/2016 | Suzuki |
| 2016/0266362 | A1* | 9/2016 | Kapanidis .......... G02B 21/0088 |
| 2018/0045944 | A1 | 2/2018 | Suzuki |
| 2018/0252648 | A1* | 9/2018 | Dohi .................... G02B 21/008 |
| 2020/0271913 | A1* | 8/2020 | Honda .................. G02B 21/26 |

FOREIGN PATENT DOCUMENTS

| | | | | | |
|---|---|---|---|---|---|
| JP | 08194160 | A | | 7/1996 | |
| JP | 2000295462 | A | * | 10/2000 | .......... G02B 21/008 |
| JP | 2004348104 | A | | 12/2004 | |
| JP | 2006174764 | A | * | 7/2006 | ............ C12M 41/36 |
| JP | 2011059205 | A | | 3/2011 | |
| JP | 2013242418 | A | | 12/2013 | |
| JP | 2014167587 | A | | 9/2014 | |
| JP | 2016012114 | A | | 1/2016 | |
| WO | WO-2014127372 | A2 | * | 8/2014 | ......... G01N 21/0303 |
| WO | 2016/185619 | A1 | | 11/2016 | |
| WO | 2017104068 | A1 | | 6/2017 | |
| WO | WO-2018041988 | A1 | * | 3/2018 | ......... G02B 21/0032 |

* cited by examiner

OBSERVATION DEVICE

BACKGROUND OF THE INVENTION

The present invention relates to an observation device used for the observation of biological cells.

Conventionally, a phase contrast microscope capable of observing a biological cell without dyeing has been used to observe the biological cell while culturing the cell. The biological cell as an observation target is cultured in an incubator capable of keeping the temperature constant. In order to observe the biological cell, the phase contrast microscope needs to be arranged in the incubator. Patent Literature 1 describes an example of a phase contrast microscope configured to be incorporable in the incubator. The phase contrast microscope is an epi-illumination phase contrast microscope, in which both an illumination optical system and an observation optical system are arranged on the same side with respect to the observation target.

Illumination light beams emitted from the illumination optical system are reflected on a reflection surface to be reflected light beams. The reflected light beams include a directly reflected light beam which is reflected on the surface of the reflection surface without being diffracted inside the observation target when passing through the observation target and a diffracted and reflected light beam which is diffracted inside the observation target when passing through the observation target to be delayed in phase by ¼ wavelength and reflected on the surface of the reflection surface. In the observation by the phase contrast microscope, the phase of the directly reflected light beam reflected on the surface of the reflection surface is advanced or delayed by ¼ wavelength. By an operation the phase of the directly reflected light beam, a phase contrast between the directly reflected light beam and the diffracted and reflected light beam is 0 or ½ wavelength and the directly reflected light beam and the diffracted and reflected light beam are intensified or weakened with each other. Since the phase contrast between the directly reflected light beam and the diffracted and reflected light beam is converted into the contrast between brightness and darkness, an optical image perceptible to human eyes is obtained.

Patent Literature 1: Japanese Patent Application Laid-Open No. 08-194160

SUMMARY OF THE INVENTION

It is not realistic from the viewpoint of cost that, when a plurality of observation targets is observed, the phase contrast microscope is provided for each observation target. Therefore, the observation target or the phase contrast microscope needs to be moved. However, when the observation target or the phase contrast microscope is moved, the distance from a phase plate to a reflection surface varies due to the limitation of the accuracy of the stop position of the observation target or the phase contrast microscope.

Herein, the phase contrast microscope has the phase plate having a phase film region in which the phase is changed by ¼ wavelength and a transmission region in which the phase is not changed. By the passage of the directly reflected light beam through the phase film region and the passage of the diffracted and reflected light beam through the transmission region, the phase of the directly reflected light beam is changed by ¼ wavelength.

In the phase contrast microscope described in Patent Literature 1, the illumination light beam emitted from the illumination optical system toward the observation target is tilted with respect to the optical axis. Therefore, when the distance from the phase plate to the reflection surface varies, a position (convergence point) where the directly reflected light beams are converged on the phase plate is changed. When the directly reflected light beam does not pass through the phase film region due to variations in the convergence point, the contrast varies, so that a good optical image obtained by the previous adjustment is not obtained. Therefore, work is required which adjusts the distance from the phase contrast microscope to the observation target, i.e., the distance from the phase plate to the reflection surface, such that the directly reflected light beam passes through the phase film region whenever the phase contrast microscope is moved, which causes a workability reduction.

The present invention has been made in view of the above-descried circumstances. It is an object of the present invention to provide an observation device capable of obtaining a good optical image by keeping contrast constant while eliminating the necessity of work for adjusting the distance from a phase plate to a reflection surface.

(1) An observation device according to the present invention includes an epi-illumination phase contrast microscope including an illumination light beam source, an illumination optical system emitting an illumination light beam from the illumination light beam source to an observation target which is a biological cell, and an observation optical system forming an optical image of the observation target from one or more reflected light beams obtained by reflection of the illumination light beam after passing through the observation target, in which the observation optical system includes a phase plate changing the phase of a directly reflected light beam reflected on the reflection surface among the reflected light beams and both the illumination optical system and the observation optical system are arranged under the observation target, an image pickup device photoelectrically converting the optical image obtained by the observation optical system to create image data of the observation target, and a display device displaying the image data, in which the illumination light beam emitted from the illumination optical system is a collimated light beam.

According to the above-described configuration, a collimated illumination light beam is emitted from the illumination optical system, and therefore collimated reflected light beams enter the observation optical system. Since the reflected light beams are parallel to the optical axis, a convergence point in the phase plate of the directly reflected light beam does not vary even when the distance from the phase plate to the reflection surface varies. Therefore, even when the distance varies by moving the epi-illumination phase contrast microscope, the contrast can be kept constant and a good optical image is obtained.

(2) Preferably, the observation device includes a moving device moving the observation target and the epi-illumination phase contrast microscope relative to each other.

According to the above-described configuration, the observation device includes the moving device, and therefore there is no necessity of manually moving the observation target or the epi-illumination phase contrast microscope. Therefore, the workability is improved.

(3) Preferably, the observation device includes an incubator including a chassis having an opening, a lid body capable of opening/closing the opening, and a partition wall partitioning the internal space defined by the chassis and the lid body into a culture chamber in the upward and a machine chamber in the downward, in which the observation target is arranged in the culture chamber, the epi-illumination phase contrast microscope, the image pickup device, and the moving device are arranged in the machine chamber, the partition wall is fixed to the chassis such that the culture chamber maintains airtightness and watertightness against the machine chamber, and at least one part of the partition wall is formed of a transparent material transmitting the illumination light beam.

According to the above-described configuration, the epi-illumination phase contrast microscope is arranged in the incubator, and therefore there is also no necessity of opening the incubator and moving the microscope to the incubator from the outside in order to observe the observation target. Therefore, there is also no necessity of maintaining the external environment of the incubator in an aseptic state so as not to cause problems even when the incubator is opened in each observation of the observation target. Hence, man hours and cost required for the observation of the incubator are reduced. Further, the airtightness and the watertightness of the culture chamber are maintained against the machine chamber, and therefore the atmosphere of the machine chamber is separated from the atmosphere of the culture chamber. Therefore, even when a temperature difference occurs between the culture chamber and the machine chamber, it is suppressed that dew condensation occurs in the epi-illumination phase contrast microscope in the machine chamber.

(4) Preferably, the illumination light beam source is configured to be able to switch the wavelength of the illumination light beam among a plurality of different wavelengths.

According to the above-described configuration, the wavelength of the illumination light beam can be switched among a plurality of different wavelengths. Therefore, the image data amount in the cell boundary of the observation targets can be reduced by shading off the obtained image and the measurement of the number of cells can be facilitated. Further, a portion formed by foreign substances, such as dust, adhering to an objective lens among parts contained in the optical image on an imaging surface is not affected by a change in the wavelength of the illumination light beam. Therefore, it can be specified by the change in the wavelength of the illumination light beam whether each part of the optical image is an image of the observation target or an image formed by the foreign substances.

(5) Preferably, the observation device includes an image processing portion correcting the image data, in which, in the image data, one or more pixels containing a luminance value as color information are arranged in two-dimensional coordinates, and the image processing portion includes a calculation portion calculating a difference between the luminance values for each of the pixels of the same coordinate with respect to two image data of the image data obtained by the illumination light beams of two different wavelengths among the wavelengths, a recognition portion recognizing the pixel having the difference smaller than a predetermined value as a noise pixel containing incorrect information, and a creation portion deleting the noise pixel from each of the two image data to create two corrected image data.

When the wavelength is changed in a case of the reflected light beam passing through the observation target, a focal position changes so as to be converged or diffused, so that the difference between the luminance values changes. Even when the wavelength is changed in a case of a reflected light beam not passing through the observation target, e.g., a reflected light beam from dust adhering to the objective lens, the focal position does not change so as to be converged or diffused and the difference between the luminance values does not change so much.

According to the above-described configuration, the pixel having the difference between the luminance values smaller than a predetermined value is recognized as the noise pixel containing incorrect information, and two corrected image data from which the noise pixels are deleted are created. Therefore, influence of the incorrect information caused by dust can be eliminated in the image data of the observation target.

(6) Preferably, the observation device includes a reflector arranged above the observation target.

According to the above-described configuration, not only the reflected light beams from the observation target but reflected light beams from the reflector enter the observation optical system. Since the amount of the light beams entering the observation optical system increases, the image data of the observation target with higher identifiability can be obtained.

(7) Preferably, the observation device includes a petri dish containing a lower dish and an upper dish formed of a translucent material and housing the biological cell, in which the reflector is fixed to the upper dish.

According to the above-described configuration, the reflector is fixed to the upper dish, and therefore the reflector can be easily arranged.

(8) Preferably, the illumination optical system includes a half mirror reflecting the illumination light beam from the illumination light beam source and a first objective lens and a second objective lens refracting the illumination light beam reflected on the half mirror and the observation optical system includes the first objective lens and the second objective lens refracting the reflected light beam from the observation target and the half mirror transmitting the refracted reflected light beam.

The observation device of the present invention can keep contrast constant while eliminating the necessity of work for adjusting the distance from a phase contrast microscope to an observation target and can obtain a good optical image.

BRIEF DESCRIPTION OF DRAWINGS

FIGS. 2A and 2B are views illustrating an incubator 11 according to this embodiment, in which

DESCRIPTION OF EMBODIMENTS

Hereinafter, preferable embodiments of the present invention are described. It is a matter of fact that this embodiment is merely one embodiment of the present invention and can be changed without changing the gist of the present invention.

[Observation Device 10]

Figure 1:
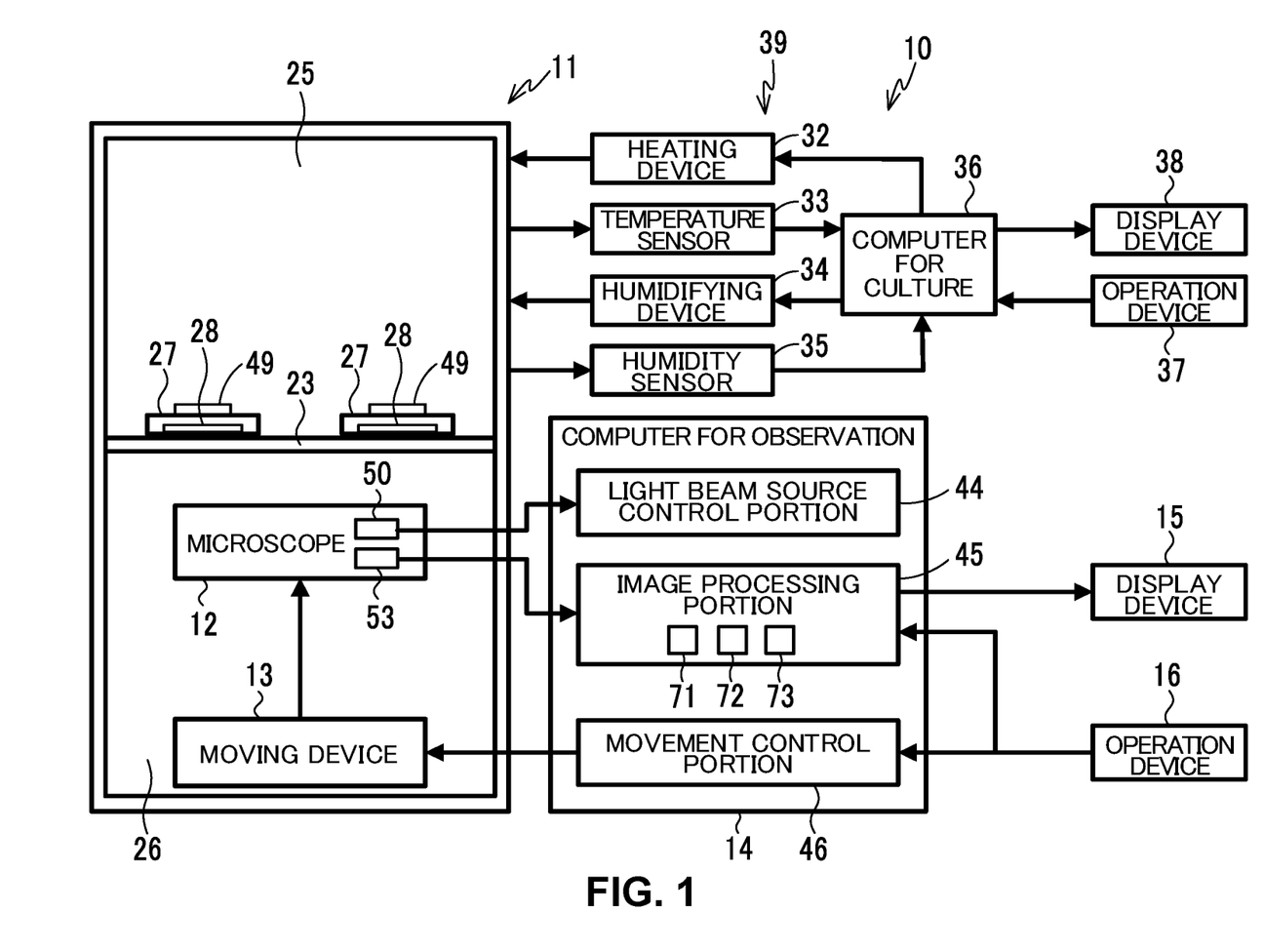
FIG. 1 is a block diagram of an observation device 10 according to this embodiment.

As illustrated in FIG. 1, an observation device 10 according to this embodiment is a device observing observation targets 28 which are biological cells. The observation device 10 includes an incubator 11, an epi-illumination phase contrast microscope (hereinafter referred to as a microscope) 12, a moving device 13, a computer for observation 14, a display device 15, and an operation device 16. The incubator 11 includes an atmosphere control mechanism 39. The microscope 12 includes an illumination light beam source 50. In the microscope 12, an image pickup device 53 is provided. The computer for observation 14 includes a light beam source control portion 44, an image processing portion 45, and a movement control portion 46.

Elements configuring the observation device 10 roughly function as follows. The illumination light beam source 50 illuminates the observation targets 28. The microscope 12 acquires an optical image of the illuminated observation target 28. The moving device 13 moves the microscope 12 such that the microscope 12 can acquire the optical image of the observation target 28. The image pickup device 53 photoelectrically converts the optical image acquired by the microscope 12 to create image data. The image processing portion 45 corrects the image data obtained by the image pickup device 53. The display device 15 displays the image data before the correction and after the correction. The movement control portion 46 controls the driving of the moving device 13. The light beam source control portion 44 controls the driving of the illumination light beam source 50. The operation device 16 can be input commands for the image processing portion 45 and can be input commands for the movement control portion 46. The operation device 16 is a keyboard and a mouse, for example. A user can operate the operation device 16 to set processing contents to the image processing portion 45 and control the movement of the microscope 12 through the driving of the moving device 13. Thus, the observation target 28 is observed by the observation device 10.

[Incubator 11]

Figure 2A:
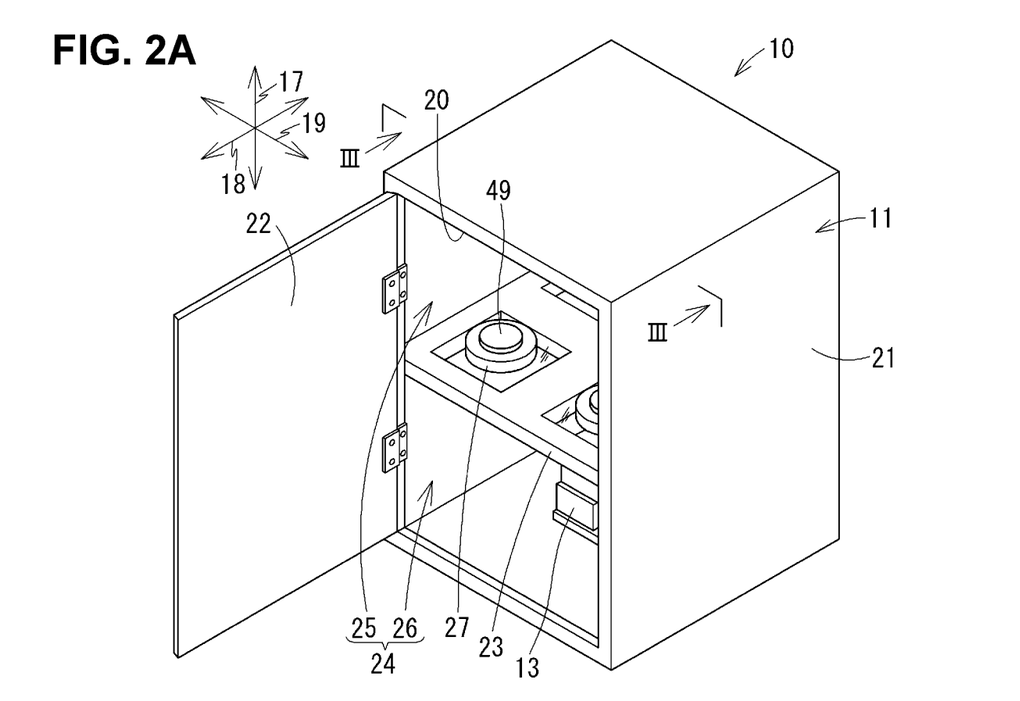
FIG. 2A is a perspective view of the incubator 11 and FIG. 2B is a perspective view illustrating a partition wall 23, a microscope 12, and a moving device 13 arranged in the incubator 11.

The incubator 11 includes a chassis 21 having an opening 20, a lid body 22 capable of opening/closing the opening 20, and a partition wall 23 arranged in the chassis 21 as illustrated in FIG. 2A. Hereinafter, a vertical direction 17, a forward and backward direction 18, and a right and left direction 19 are defined based on the attitude of the incubator 11 illustrated in FIG. 1. The opening 20 is opened in the forward and backward direction 18. An internal space 24 of the incubator 11 is defined by the chassis 21 and the lid body 22. The outer shape of the chassis 21 and the lid body 22 is a rectangular parallelepiped shape. The shape of the internal space 24 is also a rectangular parallelepiped shape. In the internal space 24, airtightness and watertightness are maintained against the open air of the incubator 11 in a state where the lid body 22 is closed.

Figure 2B:
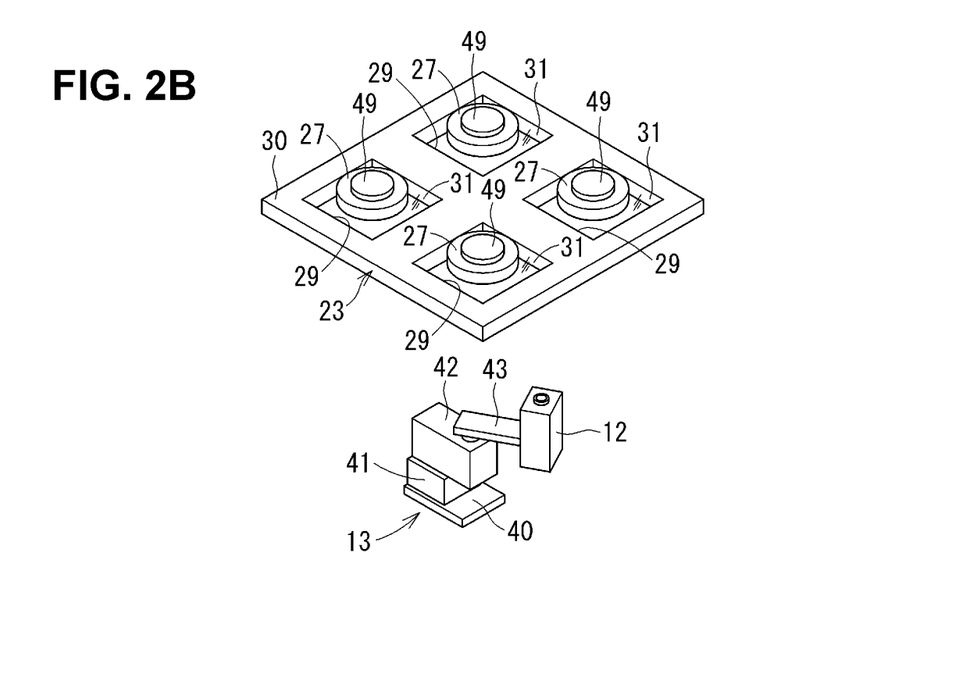

As illustrated in FIG. 2A and FIG. 2B, the partition wall 23 partitions the internal space 24 into a culture chamber 25 in the upward and a machine chamber 26 in the downward. In the culture chamber 25, four petri dishes 27 are arranged. In each petri dish 27, the observation target 28 (FIG. 3, FIG. 4) which is a biological cell is housed. In the machine chamber 26, the microscope 12 mounted with the image pickup device 53 and the moving device 13 are housed.

The partition wall 23 is a flat plate shape having a square shape as viewed from the vertical direction 17. The partition wall 23 has a frame plate 30 having four openings 29 and a transparent plate 31 fitted into each of the four openings 29. The transparent plates 31 are formed of a material transmitting a light beam, and thus can transmit a light beam in the vertical direction 17. The material of the transparent plates 31 is glass or acryl, for example. The four transparent plates 31 are located at the vertex positions of the square as viewed from the vertical direction 17.

[Petri Dish 27]

Figure 3:
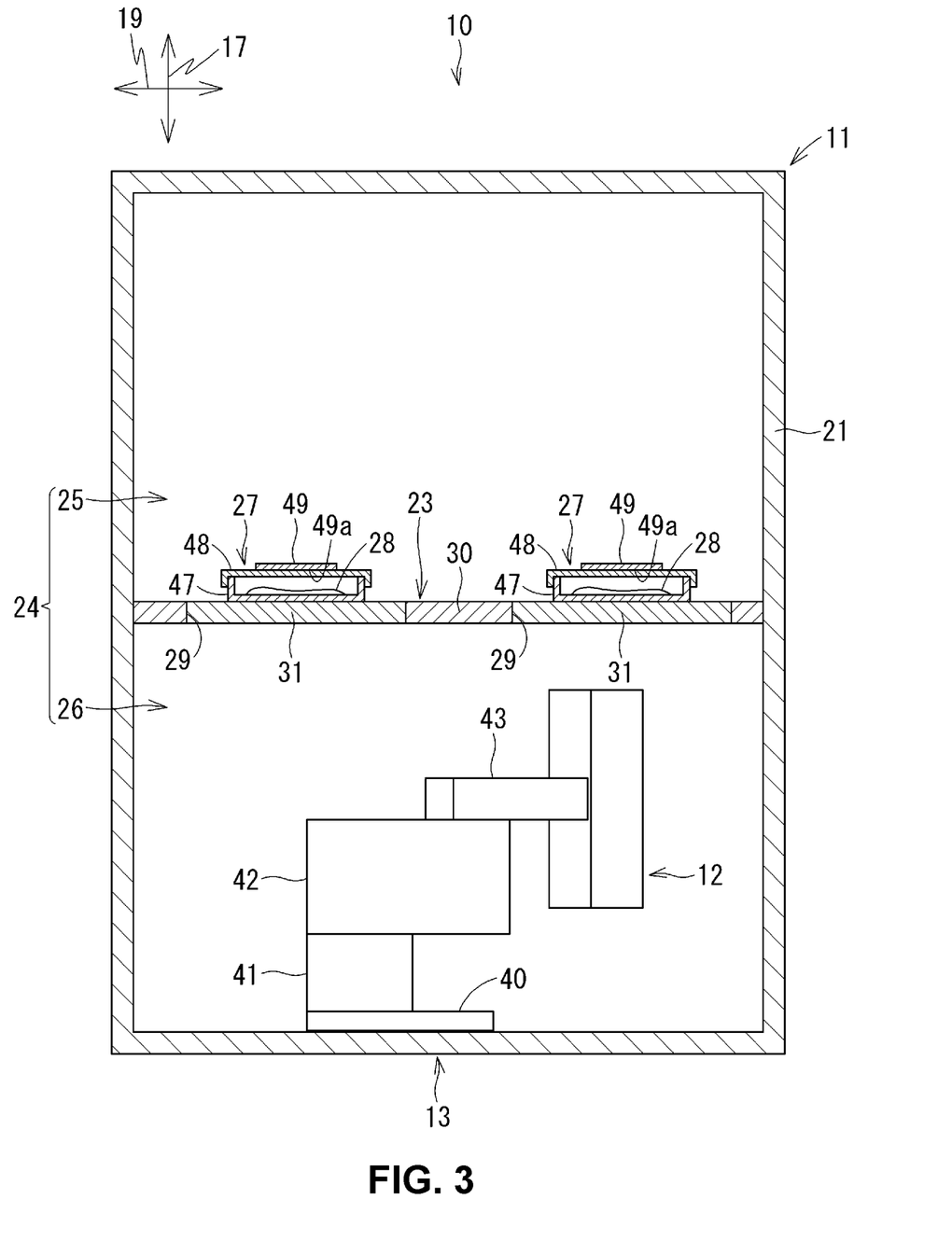
FIG. 3 is a cross-sectional view of the incubator 11 as viewed from the III-III cutting line of FIG. 2A.

As illustrated in FIG. 3, the petri dish 27 has a lower dish 47 and an upper dish 48 so as to be nested. Both the lower dish 47 and the upper dish 48 are shallow cylindrical containers having a bottom surface. The upper dish 48 is larger than the lower dish 47. By placing the lower dish 47 on the upper dish 48, the inside of the petri dish 27 is closed. Both the lower dish 47 and the upper dish 48 are formed of a material transmitting a light beam, for example, polystyrene resin.

[Reflector 49]

As illustrated in FIG. 1 to FIG. 3, the observation device 10 includes reflectors 49 reflecting illumination light beams 61 from the microscope 12. The reflector 49 is fixed to the upper surface of the upper dish 48. The reflector 49 has a disk shape. The reflector 49 is formed of stainless steel in this embodiment. A reflection surface 49a (undersurface 49a) provided on the undersurface of the reflector 49 is mirror finished so as to be able to reflect a light beam.

[Atmosphere Control Mechanism 39]

The atmosphere control mechanism 39 of the incubator 11 is described referring to FIG. 1 again. The atmosphere control mechanism 39 is a mechanism of controlling the atmosphere (temperature and humidity) of the culture chamber 25 and can control the atmosphere independently of the atmosphere of the machine chamber 26. Specifically, the atmosphere control mechanism 39 includes a heating device 32, a temperature sensor 33, a humidifying device 34, a humidity sensor 35, a computer for culture 36, an operation device 37, and a display device 38. The heating device 32 can increase the temperature of the culture chamber 25. The temperature sensor 33 can detect the temperature of the culture chamber 25. The humidifying device 34 can increase the humidity of the culture chamber 25. The humidity sensor 35 can detect the humidity of the culture chamber 25. The computer for culture 36 can control an operation of the heating device 32 and an operation of the humidifying device 34. The operation device 37 is a device capable of specifying target values of the temperature and the humidity of the culture chamber 25. The display device 38 can display the temperature detected by the temperature sensor 33, the humidity detected by the humidity sensor 35, and the target values specified by the operation device 37. The computer for culture 36 controls the operation of the heating device 32 and the operation of the humidifying device 34 such that detection values of the temperature and the humidity obtained by the temperature sensor 33 and the humidity sensor 35 are in agreement with the specified target values of the temperature and the humidity. Thus, the atmosphere of the culture chamber 25 is controlled.

[Moving Device 13]

As illustrated in FIG. 2A, FIG. 2B, and FIG. 3, the moving device 13 is a device moving the microscope 12 such that the microscope 12 is located immediately under the petri dish 27 housing the observation target 28. The moving device 13 includes a bottom portion 40, a body 41, a first arm 42, and a second arm 43. The bottom portion 40 is fixed to the chassis 21 of the incubator 11. The body 41 is fixed to the bottom portion 40 and houses a driving mechanism of driving the first arm 42 and the second arm 43 and a control mechanism. The first arm 42 and the second arm 43 are configured into articulated arms. A base end portion of the first arm 42 is coupled to the body 41 to be rotatable around the axis in the vertical direction 17. A base end portion of the second arm 43 is coupled to a tip portion of the first arm 42 to be rotatable around the axis in the vertical direction 17. To a tip portion of the second arm 43, the microscope 12 is fixed. The microscope 12 is movable by the driving of the moving device 13 in the horizontal direction, i.e., both the forward and backward direction 18 and the right and left direction 19. Therefore, the moving device 13 can move immediately under any of the four petri dishes 27 located on the upper side of the partition wall 23.

[Microscope 12]

Figure 4:
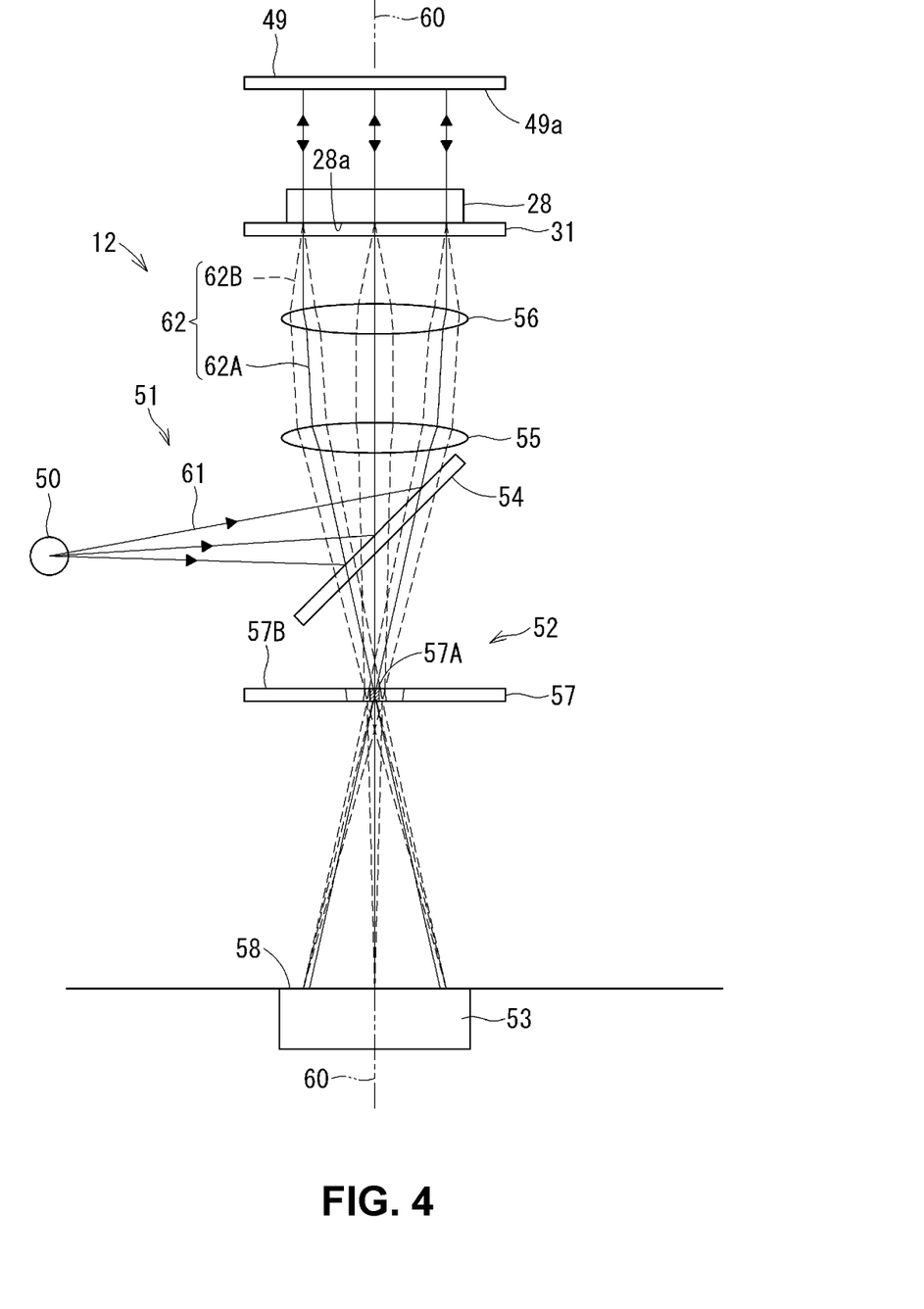
FIG. 4 is a schematic configuration diagram of the microscope 12.

The microscope 12 is described with reference to FIG. 4. The microscope 12 includes an illumination light beam source 50, an illumination optical system 51, an observation optical system 52, and an image pickup device 53. The illumination optical system 51 emits the illumination light beams 61 from the illumination light beam source 50 to the observation target 28. The observation optical system 52 forms an optical image of the observation target 28 from reflected light beams 62 generated by the reflection of the illumination light beams 61 by the reflection surface after passing through the observation target 28. The image pickup device 53 photoelectrically converts the optical image of the observation target 28 to create image data of the observation target 28.

The illumination light beam source 50 is a light beam source emitting the illumination light beams 61. The illumination light beam source 50 is a wavelength variable light beam source, and thus can change the wavelength of the illumination light beams 61. The switching of the wavelengths is performed by an operation of the operation device 16 by a user (FIG. 1). When a target value of the wavelength is specified by the operation of the operation device 16, the light beam source control portion 44 (FIG. 1) controls the illumination light beams 61 such that the illumination light beams 61 of the wavelength of the target value are emitted.

The microscope 12 is an epi-illumination microscope. The illumination optical system 51 and the observation optical system 52 are arranged on the same side with respect to the observation target 28, lower side in this embodiment. In connection therewith, the illumination light beam source 50 is also arranged on the same side (lower side) of the illumination optical system 51 and the observation optical system 52. Since the illumination optical system 51 and the observation optical system 52 are not individually arranged on each of both sides of the observation target 28, and therefore the microscope 12 is compactly configured.

The illumination optical system 51 includes a half mirror 54, a first objective lens 55, and a second objective lens 56. The half mirror 54 reflects the illumination light beams 61 from the illumination light beam source 50 and emits the illumination light beams 61 upward toward the observation position where the observation target 28 is arranged. Between the half mirror 54 and the observation target 28, the first objective lens 55 and the second objective lens 56 are arranged. The first objective lens 55 is arranged on a side close to the half mirror 54 and the second objective lens 56 is arranged on a side close to the observation target 28. The illumination light beams 61 from the half mirror 54 are refracted on the first objective lens 55 and the second objective lens 56, transmit through the transparent plate 31 and the lower dish 47 (FIG. 3), pass through the observation target 28, and then reach the reflection surface 49a. An optical axis 60 is a center axis of a luminous flux of the illumination light beams 61 emitted from the half mirror 54 and is also a center axis of the first objective lens 55 and the second objective lens 56. The optical axis 60 is along the vertical direction 17.

The illumination light beams 61 emitted from the second objective lens 56 are collimated light beams parallel to the optical axis 60. The refractive index and the arrangement of the first objective lens 55 and the second objective lens 56 are set such that such collimated light beams are emitted.

The illumination light beams 61 pass through the observation target 28, and then reflected on the reflection surface 49a to be the reflected light beams 62. The reflected light beams 62 include directly reflected light beams 62A which are not diffracted inside the observation target 28 when passing through the observation target 28 after reflected on the reflection surface 49a of the reflector 49 and diffracted and reflected light beams 62B which are reflected on the reflection surface 49a of the reflector 49, and then diffracted inside the observation target 28 when passing through the observation target 28 to be delayed in phase by ¼ wavelength. In FIG. 4, the illumination light beams 61 are illustrated by the solid lines, the directly reflected light beams 62A are illustrated by the solid lines, and the diffracted and reflected light beams 62B are illustrated by the dashed lines. The reflected light beams 62 collectively refer to the directly reflected light beam 62A and the diffracted and reflected light beam 62B.

In this embodiment, the reflector 49 is arranged above the observation target 28, and therefore the light beam amount of the reflected light beams 62 increases due to the reflection of a larger number of light beams on the reflection surface 49a of the reflector 49. The directly reflected light beams 62A are light beams passing through the observation target 28 twice before and after the reflection and not diffracted in the observation target 28 among light beams reflected on the reflection surface 49a of the reflector 49. The diffracted and reflected light beams 62B are light beams passing through the observation target 28 twice before and after the reflection and diffracted in the observation target 28 among light beams reflected on the reflection surface 49a of the reflector 49.

The observation optical system 52 includes the first objective lens 55, the second objective lens 56, the half mirror 54, a phase plate 57, and an imaging surface 58. The imaging surface 58 is a light beam receiving surface formed on the surface of the image pickup device 53 in this embodiment. Herein, the first objective lens 55 and the second objective lens 56 and the half mirror 54 are shared between the illumination optical system 51 and the observation optical system 52. The reflected light beams 62 reflected on the reflection surface 49a are refracted on the first objective lens 55 and the second objective lens 56 via the transparent plate 31 and the lower dish 47 (FIG. 3), transmit through the half mirror 54 and the phase plate 57, and then reach the imaging surface 58.

The phase plate 57 has a phase film region 57A where a phase is shifted and a transmission region 57B where a phase is not changed. The phase film region 57A is a circular region around the optical axis 60 in the phase plate 57. The transmission region 57B is an annular region around the optical axis 60 in the phase plate 57 and is located on the outside of the phase film region 57A. The phase film region 57A and the transmission region 57B are formed of a material transmitting a light beam. When a light beam passes through the phase film region 57A, the phase of the light beam is shifted by ¼ wavelength. In this embodiment, the phase is delayed by ¼ wavelength but conversely the phase may be advanced by ¼ wavelength. On the other hand, the transmission region 57B does not change the phase of a light beam passing through the transmission region 57B.

The refractive index and the arrangement of the first objective lens 55 and the second objective lens 56 and the size (radius) of the phase film region 57A are set such that the directly reflected light beams 62A pass through the phase film region 57A among the reflected light beams 62. Therefore, the phase of the directly reflected light beams 62A are shifted in the phase film region 57A. On the other hand, the diffracted and reflected light beams 62B pass through the transmission region 57B, and therefore the phase of the diffracted and reflected light beams 62B is not changed. Since the phase of the directly reflected light beams 62A is delayed by ¼ wavelength, the phase contrast between the directly reflected light beams 62A and the diffracted and reflected light beams 62B becomes 0 after passing through the phase plate 57. When the phase of the directly reflected light beams 62A is advanced by ¼ wavelength, the phase contrast between the directly reflected light beams 62A and the diffracted and reflected light beams 62B becomes ½ wavelength after passing through the phase plate 57.

A luminous flux of the reflected light beams 62 reflected after passing through each position of the observation target 28 is converged on the imaging surface 58. When the phase of the directly reflected light beams 62A is delayed by ¼ wavelength, the directly reflected light beams 62A and the diffracted and reflected light beams 62B are intensified with each other on the imaging surface 58. Therefore, an optical image with bright contrast is obtained in which the observation target 28 is bright and the background is dark. When the phase of the directly reflected light beams 62A is advanced by ¼ wavelength, an optical image with dark contrast is conversely obtained in which the observation target 28 is dark and the background is bright.

The optical image formed on the imaging surface 58 is photoelectrically converted by the image pickup device 53, and then image data is created. The image data is corrected in the image processing portion 45 (FIG. 1), and then displayed on the display device 15.

[Image Processing Portion 45]

The image processing portion 45 is described referring to FIG. 1 again. The image processing portion 45 has a filter function of removing noise information with respect to the image data obtained by the image pickup device 53. This filter function is a function of removing noise information due to dust adhering to the second objective lens 56 or the like from the image data based on two image data obtained by the illumination light beams 61 of two different wavelengths.

The change in the wavelength of the illumination light beams 61 is equal to a change in the optical path length from the observation target 28 to the imaging surface 58. By this change, the position where the reflected light beams 62 are converged varies. When the reflected light beams 62 are converged on the imaging surface 58, the optical image is focused. However, when the reflected light beams 62 are not converged on the imaging surface 58, the optical image is not focused. More specifically, focused image data and not-focused image data are created by the illumination light beams 61 of two different wavelengths. Herein, the optical image formed by dust adhering to the second objective lens 56 or the like is not affected by the variation in the optical path length, and therefore the luminance does not vary. Then, pixels of a portion where the variation in the luminance is relatively small are specified in the two image data obtained by the change in the wavelength, whereby the noise information contained in the image data can be specified. Further, information of the pixels containing the noise information is deleted, whereby the image data from which the noise information is deleted can be created.

Before the image processing portion 45 is caused to exhibit the filter function, the light beam source control portion 44 controls the illumination light beam source 50, so that the wavelength of the illumination light beams 61 is changed. Thus, image data obtained by the illumination light beams 61 of a first wavelength and image data obtained by illumination light beams of a second wavelength are obtained. Herein, the image data is an aggregate of the pixels arranged in two-dimensional coordinates. Each pixel has information of a luminance value as color information.

The image processing portion 45 includes a calculation portion 71, a recognition portion 72, and a creation portion 73. The calculation portion 71 calculates the difference between the luminance values for each pixel of the same coordinate with respect to the two image data obtained by the illumination light beams 61 of the two different wavelengths. The recognition portion 72 recognizes a pixel where the difference is smaller than a predetermined value as a noise pixel containing incorrect information. The creation portion 73 deletes the noise pixels from each of the two image data to create two corrected image data. Thus, the presence or absence of the noise information contained in the image data is recognized and further the image data from which the noise information is deleted is created.

[Operational Effects of Embodiment]

According to the observation device 10 of this embodiment, the collimated illumination light beams 61 are emitted from the illumination optical system 51, and therefore the collimated reflected light beams 62 enter the observation optical system 52. The reflected light beams 62 are parallel to the optical axis 60, and therefore, even when the distance from the microscope 12 to the observation target 28 varies, the convergence point in the phase plate 57 of the directly reflected light beams 62A does not vary. Therefore, even when the distance varies by moving the microscope 12, the contrast can be kept constant and a good optical image is obtained.

Further, the observation device 10 includes the moving device 13, and therefore there is no necessity of manually moving the observation targets 28 or the microscope 12. Therefore, the workability is improved.

Further, the microscope 12 is arranged in the incubator 11, and therefore there is no necessity of opening the incubator 11 and moving the microscope 12 to the incubator 11 from the outside in order to observe the observation targets 28. Therefore, there is also no necessity of maintaining the external environment of the incubator 11 in an aseptic state so as not to cause problems even when the incubator 11 is opened in each observation of the observation targets 28. Hence, man hours and cost required for the observation of the incubator 11 are reduced. Further, the airtightness and the watertightness of the culture chamber 25 are maintained against the machine chamber 26, and therefore the atmosphere of the machine chamber 26 is separated from the atmosphere of the culture chamber 25. Therefore, even when a temperature difference occurs between the culture chamber and the machine chamber, it is suppressed that dew condensation occurs in the epi-illumination phase contrast microscope in the machine chamber.

Further, the wavelength of the illumination light beams 61 is switchable between a plurality of different wavelengths. Therefore, the image data amount in the cell boundary of the observation targets 28 can be reduced by shading off the obtained image and the measurement of the number of cells can be facilitated. Further, a portion formed by foreign substances, such as dust, adhering to the second objective lens 56 among parts contained in the optical image on the imaging surface 58 is not affected by a change in the wavelength of the illumination light beams 61. Therefore, it can be specified by the change in the wavelength of the illumination light beams 61 whether each part of the optical image is an image of the observation target 28 or an image formed by the foreign substances.

Further, the pixel having the difference between the luminance values smaller than a predetermined value is recognized as the noise pixel containing incorrect information and two corrected image data from which the noise pixels are deleted are created. Hence, influence of the incorrect information caused by dust can be eliminated in the image data of the observation target 28.

Further, the reflected light beams 62 from the observation target 28 and the reflected light beams 62 from the reflector 49 enter the observation optical system 52. Since the amount of the light beams entering the observation optical system 52 increases, the image data of the observation target 28 with higher identifiability can be obtained.

Further, the reflector 49 is fixed to the upper dish 48, and therefore the reflector 49 can be easily arranged.

[Modification]

In this embodiment, the moving device 13 is a device moving the microscope 12 but is not limited to this configuration. The moving device 13 may be a device moving the observation target 28 and the microscope 12 relative to each other. The moving device 13 may be a device moving the observation targets 28 instead of moving the microscope 12. Further, the moving device 13 is provided in order to automatically move the microscope 12 in this embodiment. When the moving device 13 is not an indispensable constituent component and the microscope 12 or the observation targets 28 are manually moved, the moving device 13 may not be provided.

In this embodiment, the reflector 49 provided with the reflection surface 49a on the undersurface is provided. The reflector 49 is not an indispensable constituent component and the reflector 49 may not be provided. In this case, an optical image of the observation target 28 is formed in the microscope 12 based on the reflected light beams 62 reflected on the surface of another reflection surface after passing through the observation target 28. For example, the undersurface of the upper dish 48 or the undersurface of the lower dish 47 when the lower dish 47 is further placed on the upper side in the vertical direction 17 of the upper dish 48 in FIG. 3, for example, can also be utilized as the reflection surface similarly to the reflection surface 49a.

In this embodiment, the reflector 49 is a plate material fixed to the upper dish 48 of the petri dish 27 but is not limited to this configuration. The reflector 49 may be arranged above the observation target 28 and be able to reflect the illumination light beams 61. A position where the reflector 49 is arranged or a target to which the reflector 49 is fixed is not limited. The reflector 49 may be arranged in the culture chamber 25 and fixed to the chassis 21 of the incubator 11.

In this embodiment, by switching the wavelength of the illumination light beams 61 among a plurality of different wavelengths, an image to be obtained can be shaded off and image data of foreign substances, such as dust, can be extracted. However, by switching the wavelength of the illumination light beams 61 to a different wavelength without being limited thereto, the distance between a phase plate and a reflection surface can also be adjusted, the position (convergence point) where directly reflected light beams are converged on the phase plate can also be changed, and an imaging surface can also be focused.

DESCRIPTION OF REFERENCE NUMERALS

10 observation device
11 incubator
12 epi-illumination phase contrast microscope (microscope)
13 moving device
15 display device
20 opening
21 chassis
22 lid body
23 partition wall
24 internal space
25 culture chamber
26 machine chamber
27 petri dish
28 observation target
45 image processing portion
47 lower dish
48 upper dish
49 reflector
49a reflection surface (undersurface of reflector)
50 illumination light beam source
51 illumination optical system
52 observation optical system
53 image pickup device
61 illumination light beam
62 reflected light beam
71 calculation portion
72 recognition portion
73 creation portion

The invention claimed is:

1. An observation device comprising:
an epi-illumination phase contrast microscope including an illumination light beam source, an illumination optical system emitting an illumination light beam from the illumination light beam source to an observation target which is a biological cell, and an observation optical system forming an optical image of the observation target from one or more reflected light beams obtained by reflection of the illumination light beam after passing through the observation target;
a moving device moving the epi-illumination phase contrast microscope relative to the observation target, the illumination optical system and the observation optical system being configured to be moved integrally by the moving device;
the observation optical system including a phase plate changing a phase of a directly reflected light beam reflected on a reflection surface among the reflected light beams;
both the illumination optical system and the observation optical system being arranged under the observation target;
an image pickup device photoelectrically converting the optical image obtained by the observation optical system to create image data of the observation target;
a display device displaying the image data,
wherein the illumination light beam emitted from the illumination optical system and passing through the observation target is a collimated light beam which is parallel to optical axes of the illumination optical system and the observation optical system; and an incubator including a chassis having an opening, a lid body capable of opening/closing the opening, and a partition wall partitioning an internal space defined by the chassis and the lid body into a culture chamber in an upper portion of the internal space and a machine chamber in a lower portion of the internal space, wherein the observation target is arranged in the culture chamber, the illumination light beam source, the illumination optical system and the observation optical system, including a first objective lens, a second objective lens, the phase plate, and a half mirror, along with the image pickup device, and the moving device are arranged in the machine chamber, the partition wall is fixed to the chassis such that the culture chamber maintains airtightness and watertightness against the machine chamber, and at least one part of the partition wall is formed of a transparent material transmitting the illumination light beam.

2. The observation device according to claim 1, wherein the illumination light beam source is configured to be able to switch a wavelength of the illumination light beam among a plurality of different wavelengths.

3. The observation device according to claim 2 comprising:

an image processing portion correcting the image data, wherein in the image data, one or more pixels containing a luminance value as color information are arranged in two-dimensional coordinates, and the image processing portion includes:

a calculation portion calculating a difference between the luminance values for each of the pixels of a same coordinate with respect to two image data of the image data obtained by the illumination light beams of two different wavelengths among the wavelengths;

a recognition portion recognizing the pixel having the difference smaller than a predetermined value as a noise pixel containing incorrect information; and a creation portion deleting the noise pixel from each of the two image data to create two corrected image data.

4. The observation device according to claim 2, further comprising a computer for image processing to determine whether image data of the obtained optical image is a part of the observation target or is formed by foreign substances by comparing image data for different wavelengths of the illumination light beams.

5. The observation device according to claim 1, comprising:

a reflector arranged above the observation target.

6. The observation device according to claim 5 comprising:

a petri dish containing a lower dish and an upper dish formed of a translucent material and housing the biological cell, wherein the reflector is fixed to the upper dish.

7. The observation device according to claim 5, comprising:

a petri dish containing a lower dish and an upper dish formed of a translucent material and housing the biological cell, and wherein the reflector is distinct from the petri dish, is attached to an upper outer surface of the upper dish, and reflects the illumination light beam after passing through the observation target to provide the reflected light beams.

8. The observation device according to claim 1, wherein the illumination optical system includes a half mirror reflecting the illumination light beam from the illumination light beam source and a first objective lens and a second objective lens refracting the illumination light beam reflected on the half mirror, and the observation optical system includes the first objective lens and the second objective lens refracting the reflected light beam from the observation target and the half mirror transmitting the refracted reflected light beam to the image pickup device via only a phase film region of the phase plate.

9. The observation device according to claim 1, wherein a half mirror common to the illumination optical system and observation optical system receives the illumination light beam and the one or more reflected light beams; and wherein the directly reflected light beam exiting the half mirror toward the phase plate has a light path consisting of only the phase plate and open space before impinging on the image pickup device.

10. The observation device according to claim 1, wherein the moving device is configured to move the illumination optical system and the observation optical system in only two dimensions, so as to be moved horizontally relative to the partition wall.

11. The observation device according to claim 1, wherein the one or more reflected light beams obtained by the reflection of the illumination light beam after passing through the observation target and entering the observation optical system include, as the directly reflected light beam, another collimated light beam which is parallel to the optical axes of the illumination optical system and the observation optical system.

* * * * *